US00PP09279P

United States Patent [19]

Laver

[11] Patent Number: Plant 9,279

[45] Date of Patent: Sep. 12, 1995

[54] MINIATURE ROSE PLANT NAMED 'LAVSNOWER'

[75] Inventor: Keith G. Laver, Ontario, Canada

[73] Assignee: Bear Creek Gardens, Inc., Medford, Oreg.

[21] Appl. No.: 293,550

[22] Filed: Aug. 22, 1994

[51] Int. Cl.[6] ..... A01H 5/00

[52] U.S. Cl. ..... Plt./8.1

[58] Field of Search ..... Plt. 7.1, 8.1, 8.2

[56] References Cited

U.S. PATENT DOCUMENTS

P.P. 5,111 9/1983 Moore ..... Plt./8.1
P.P. 8,742 5/1994 Laver ..... Plt./8.1

OTHER PUBLICATIONS

Brickell, et al., ed. 1980, "International code of nomenclature for cultivated plants–1980," Bohn, Scheltema, & Holkema, Utrecht dr. W. Junk, b.v., Publishers, The Hague. 26 pages.

Modern Roses 9, 1986, The American Rose Society, Shreveport, Louisiana, p. 166.

*Primary Examiner*—Howard J. Locker
*Attorney, Agent, or Firm*—Klarquist Sparkman Campbell Leigh & Whinston

[57] ABSTRACT

A miniature rose plant having the unique combination of its high petal count; attractive, near-white flowers; dark green foliage; and easy propagation from softwood cuttings.

1 Drawing Sheet

1

The present invention relates to a new and distinct variety of rose plant of the miniature class which was originated by me by crossing the variety Loving Touch with the variety June Laver.

The primary objective of this breeding was to produce a new rose variety having a compact, well-branched habit that would force as well as a pot rose. The color desired was anywhere from white to light yellow. These objectives were substantially achieved, along with other desirable improvements, as evidenced by the following unique combination of characteristics that are outstanding in the new variety and that distinguish it from its parents, as well as from all other varieties of which I am aware:

1. Dark green, mildew-resistant foliage;
2. Easiness to propagate from softwood cuttings; and
3. Attractive near-white flowers with a high petal count.

Asexual reproduction of this new variety by softwood cuttings, as performed at Wasco and Somis, Calif., shows that the foregoing characteristics and all other features come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—Loving Touch.

*Pollen parent.*—June Laver.

Classification:

*Botanical.*—*Rosa hybrida.*

*Commercial.*—Miniature.

2

FLOWER

Observations made from specimens grown in a greenhouse environment at Somis, Calif., from January to April 1994.

Blooming habit: Recurrent.

Bud:

*Size.*—$\frac{1}{2}$ inch long when the petals start to unfurl.

*Form.*—The bud form is short, pointed ovoid.

*Color.*—When sepals first divide, bud color is Yellow-White Group 158C. When half blown, the upper sides of the petals are Yellow-White Group 158D except in the flower center where it is Yellow-White Group 158B; and the lower sides of the petals are Yellow-White Group 158D.

*Sepals.*—Color: Green Group 138A. Surface texture: Covered in fine hairs. There are three lightly appendaged sepals. There are two unappendaged sepals with hairy edges.

*Receptacle.*—Color: Green Group 137A. Shape: Funnel. Size: Small ($\frac{1}{8}$ inch$\times\frac{1}{8}$ inch). Surface: Smooth.

*Peduncle.*—Length: Short ($\frac{1}{2}$–$\frac{3}{4}$ inch). Surface: Smooth. Color: Medium Green. Strength: Stiff, erect, slender.

Bloom:

*Size.*—Small. Average open size is $1\frac{1}{4}$ to $1\frac{1}{2}$ inches.

*Borne.*—Singly.

*Stems.*—Short, strong. Average length is about 4 to 6 inches.

*Form.*—When first open: High centered. Permanence: Flattens, all petals curl, quill fashion.

*Petalage.*—Number of petals under normal conditions: 40 to 50.

*Color.*—The upper sides of the petals are Yellow-White Group 158D. The reverse sides of the petals are Yellow-White Group 158D. The base of each petal has a small greenish-white half-moon at the point of attachment. The major color on the upper sides of the petals is Yellow-White Group 158D.

*Variegations.*—None.

*Discoloration.*—The general tonality at the end of the first day: No change. At the end of the third day: No change.

*Fragrance.*—Slight.

Petals:

*Texture.*—Thin.

*Shape.*—Oval.

*Form.*—Tips slightly recurved, edges slightly quilled.

*Arrangement.*—Imbricated, with a few petaloids in the center.

*Persistence.*—Drop off cleanly.

*Lastingness.*—On the plant: Fair (7 to 8 days).

Reproductive parts:

*Anthers.*—Size: Small. Quantity: Few. Color: Yellow. Arrangement: Regular around styles.

*Filaments.*—Color: Yellow.

*Pollen.*—Color: Lemon yellow.

*Styles.*—Color: Reddish.

*Stigmas.*—Color: Greenish white.

Form: Bush.

Growth: Vigorous, dwarf, upright, branching, compact. Size at maturity is 10 to 12 inches in height.

Foliage: Number of leaflets on normal mid-stem leaves: 5.

*Size.*—Small ($1\frac{3}{4}$ to 2 inches$\times$1 inch).

*Quantity.*—Normal.

*Color.*—New foliage: Green Group 137C. Old foliage: Green Group 137A.

Leaflets:

*Shape.*—Pointed oval.

*Texture.*—Upper side: Smooth.

*Edge.*—Serrated.

*Serration.*—Single, small.

*Petiole rachis.*—Color: Green.

*Petiole underside.*—Smooth.

*Stipules.*—Short, serrated, bearded.

*Disease resistance.*—Resistant to mildew under normal greenhouse growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Short, straight to hooked slightly downward.

*Color when young.*—Red.

Small prickles:

*Quantity.*—On main stalks: None. On laterals: None.

I claim:

1. A new and distinct variety of rose plant of the miniature class, substantially as herein shown and described, characterized particularly as to novelty by the unique combinaiton of its high petal count, attractive, near-white flowers; dark green foliage; and easy propagation from softwood cuttings.

* * * * *

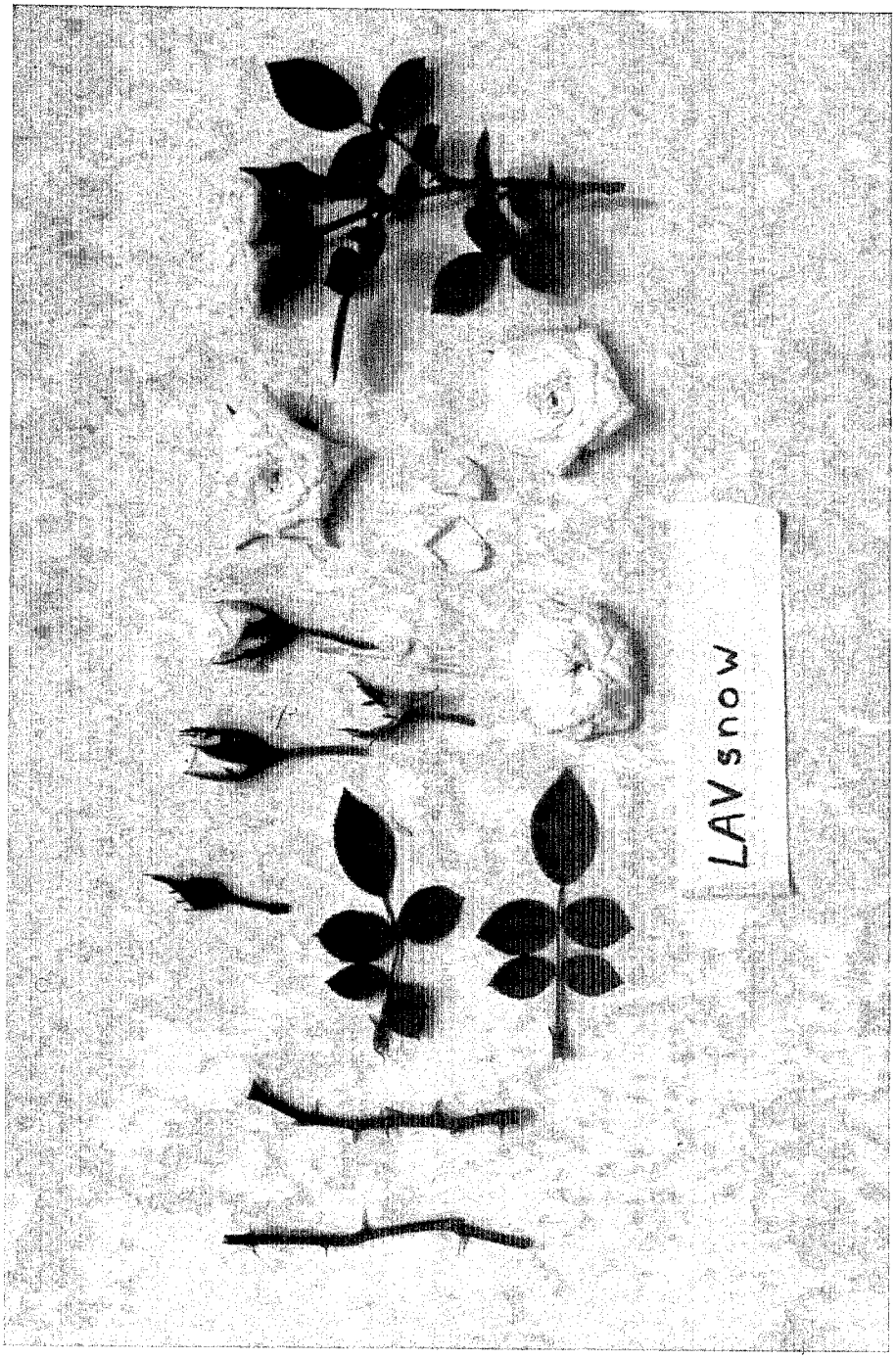
LAV snow